United States Patent [19]

Medvid

[11] Patent Number: 4,711,264
[45] Date of Patent: Dec. 8, 1987

[54] PLUG VALVE

[75] Inventor: Richard J. Medvid, Cookeville, Tenn.

[73] Assignee: The Duriron Company, Inc., Dayton, Ohio

[21] Appl. No.: 930,195

[22] Filed: Nov. 13, 1986

[51] Int. Cl.$^4$ .......................... B08B 3/00; B08B 9/00; F16K 51/00
[52] U.S. Cl. .................................. 137/241; 137/240; 134/166 C; 222/148; 251/309; 251/312
[58] Field of Search .................. 134/166 C; 137/240, 137/241, 375; 222/148; 251/309, 310, 312, 317

[56] References Cited

U.S. PATENT DOCUMENTS

| | | | |
|---|---|---|---|
| 646,104 | 3/1900 | Faber | 137/240 |
| 1,400,647 | 12/1921 | Westinghouse | 137/246.21 |
| 1,734,569 | 11/1929 | Godfrey | 137/241 |
| 1,839,092 | 12/1931 | Feldmeier et al. | 137/241 |
| 1,840,100 | 1/1932 | Jacobsen | 137/241 |
| 1,954,217 | 4/1934 | Morrow | 137/241 |
| 2,372,920 | 4/1945 | Wiles | 137/239 |
| 2,466,790 | 4/1949 | Bettcher | 251/93 |
| 2,467,313 | 4/1949 | Jacobsen | 251/93 |
| 2,518,790 | 8/1950 | Jacobsen | 251/93 |
| 3,206,163 | 9/1965 | Freed | 251/309 |
| 3,359,062 | 12/1967 | Palm | 21/56 |
| 3,498,318 | 3/1970 | Duffey | 137/375 |
| 4,003,703 | 1/1977 | Montgomery et al. | 21/56 |
| 4,324,762 | 4/1982 | Redikultsev et al. | 422/106 |
| 4,547,339 | 10/1985 | McClure | 422/26 |
| 4,559,967 | 12/1985 | Gardner et al. | 137/340 |

Primary Examiner—George L. Walton
Attorney, Agent, or Firm—Biebel, French & Nauman

[57] ABSTRACT

A plug valve which may be steam sterilized in place, without disassembly or removal from the system, is adapted for use in fermentation processes where the interior surfaces must be sterilized between batches. The plug is provided with internal steam passages which extend longitudinally of the plug and in non-intersecting relation to the through port. The plug casing, in one embodiment, is provided with an inlet for applying steam to the top of the plug for entrance into the steam passages and out the bottom of the plug and through a bottom opening in a casing. In another embodiment, steam may be applied through the bottom opening and into the plug passages, and a steam outlet is provided in the face of the plug through which steam may be extracted through one of the valve casing ports.

3 Claims, 7 Drawing Figures

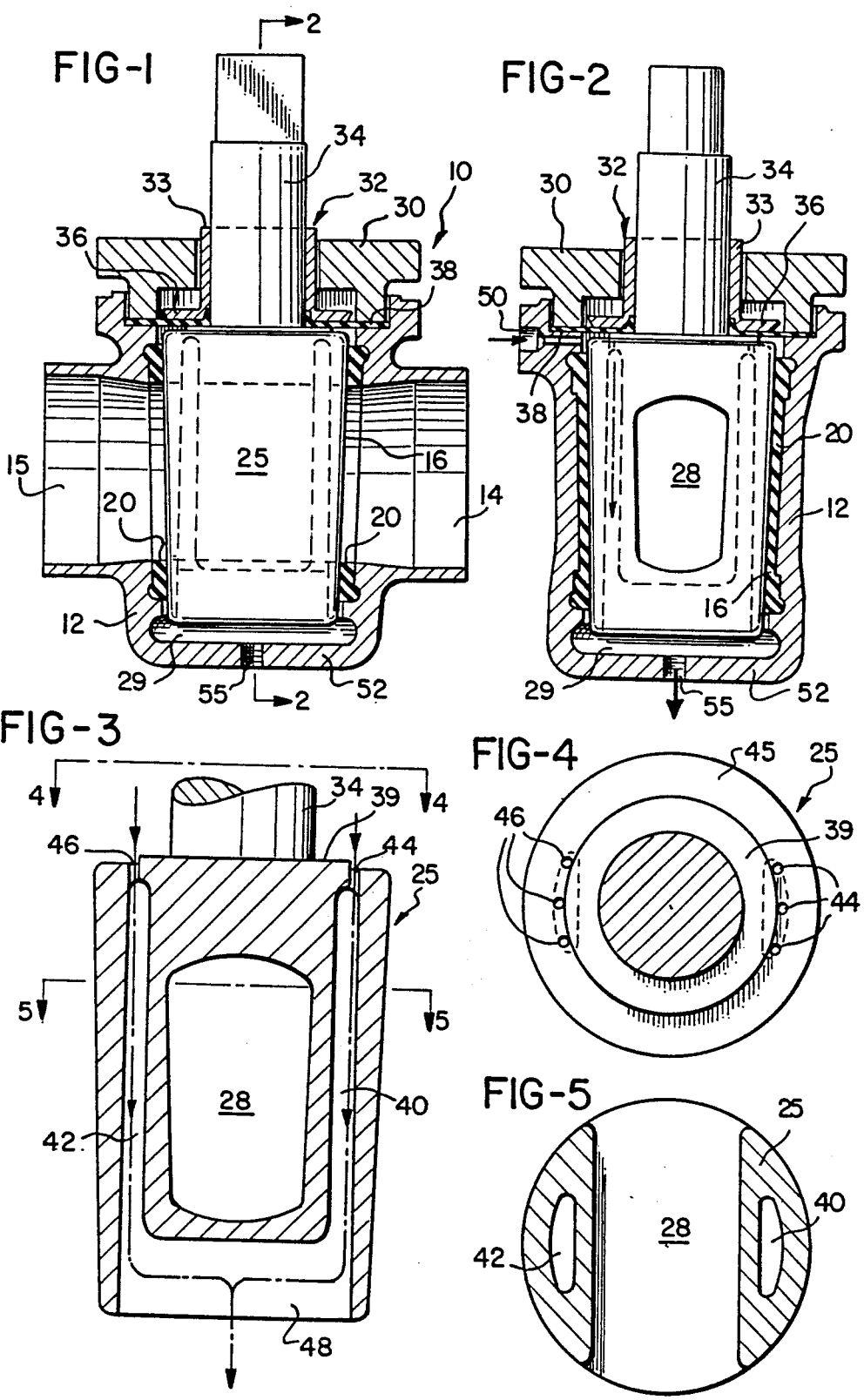

4,711,264

PLUG VALVE

This invention relates to plug valves and more particularly to a plug valve which may be sterilized in place, and without disassembly.

BACKGROUND OF THE INVENTION

In fermentation processes, there is a need to provide correct and accurate control of bacteria, for each batch processed. For this reason, the equipment used in the process must be thoroughly cleaned and sterilized prior to its use with each new batch, after which the desired bacteria and food are introduced. Valves commonly used in such processes must be removed from the fermentation unit, disassembled, cleaned, sterilized, and reinstalled. A valve which can be cleaned and sterilized in place would permit increased production at decreased cost.

The cleaning and sterilizing media for fermentation equpment is universally steam. It would be desirable to provide a valve in which such steam may be admitted for the purpose of cleaning and sterilizing the interior surfaces, as required, without disassembly of the valve.

SUMMARY OF THE INVENTION

This invention relates to a plug valve, in which the plug is provided with discrete passageways, separate and isolated from the through port, including ports in the valve casing through which steam or other sterilizing fluid may be applied to the plug for the purpose of cleaning and sterilizing.

The invention is directed to a plug valve which may be cleaned without disassembly and without removal from the line. The plug valve is provided with a casing which has a conventional plug cavity defining inlet and outlet ports which open into cavity, and a plug is received in the cavity which has a conventional through port selectively alignable with the ports in the casing.

The plug is provided with a plurality of steam passages which extend generally longitudinally of the plug and in non-intersecting but adjacent relation to the through port, providing for the conduction of sterilizing steam to the interior of the plug. The through passages are in communication with steam inlet and outlet openings in the casing, by means of which sterilizing steam may be applied to and removed from the interior of the plug. The plug is heated by conduction which sterilizes the interior plug and valve surfaces. The interior body surfaces of the valve, inaccessible to direct steam contact, are heated by conduction and are thus sterilized.

In a first embodiment, steam is admitted and applied to an upper surface of the plug, and exits through outlets formed in the bottom of the plug through an opening in the valve casing. In a second embodiment, the steam exits from the interior of the plug through a side or wall opening for discharge downstream through one of the casing valve ports. In this embodiment, the valve and the adjoining pipe line can both be sterilized.

It is accordingly an important object of this invention to provide a plug valve which is adapted for steam sterilization without disassembly.

A further object of the invention is the provision of a plug valve, as outlined above, incorporating a plug defining or having steam passages which extend generally longitudinally of the axis of the plug and in non-intersecting relation to the port.

These and other objects and advantages of the invention will be apparent from the following description, the accompanying drawings, and the appended claims.

BRIEF DESCRIPTION OF THE DRAWINGS

FIG. 1 is a vertical section through one embodiment of a plug valve according to this invention, showing the valve plug in elevation;

FIG. 2 is a vertical section through the plug valve of FIG. 1 taken generally along the line 2—2 of FIG. 1, showing the plug in elevation;

FIG. 3 is a vertical section through the valve plug of the embodiment of FIGS. 1 and 2.;

FIG. 4 is a transverse section looking through the plug generally along the line 4—4 of FIG. 3;

FIG. 5 is a transverse section through the plug looking generally along the line 5—5 of FIG. 3;

DESCRIPTION OF THE PREFERRED EMBODIMENTS

Figure 6:
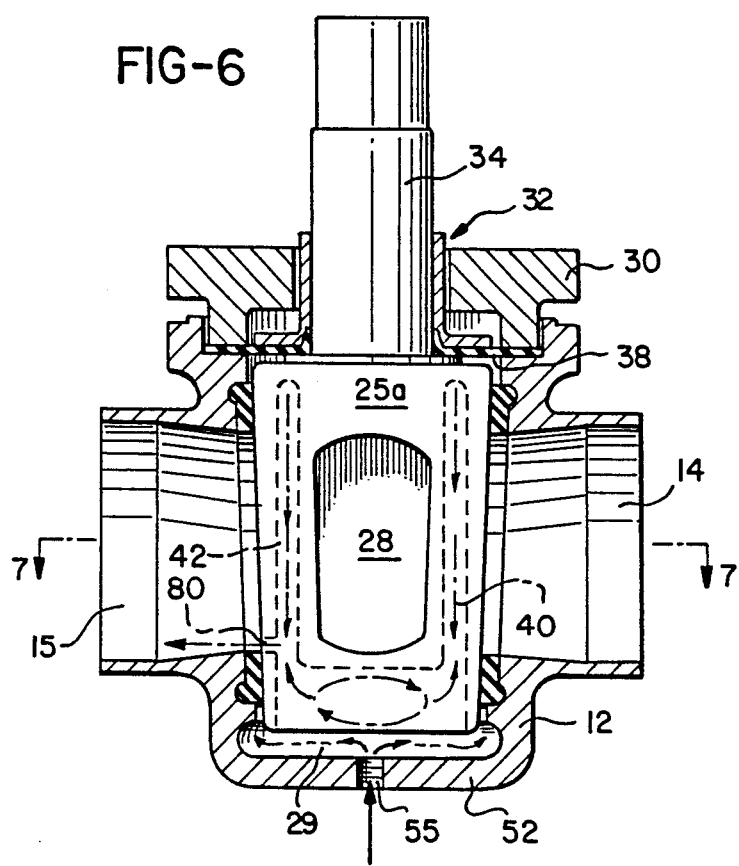
FIG. 6 is a vertical section similar to FIG. 1 of a modified form of the plug valve according to this invention.

Referring to the drawings which illustrate preferred embodiments of the invention, a plug valve made according to this invention is illustrated generally at 10 in FIG. 1 as including a body or casing 12 which has an inlet port 14 and an outlet port 15, the ports 14 and 15 respectively opening into a tapered plug cavity 16. The cavity 16 is provided with the usual liner or sleeve 20, for sealing purposes, which may be made of PTFE or other suitable polymer.

A corresponding tapered plug 25 is received in the cavity 16. The plug 25 is provided with a through port 28 (FIG. 2) providing communication between the inlet and outlet, according to the rotational position of the plug within the casing. The sleeve or liner 20 provides the seal means which isolates the ports 14 and 15 with respect to the plug and with respect to each other, as well known and understood in the art. A clearance space 29 is formed between the bottom of the plug and the case 12.

The plug valve conventionally includes a top cap 30, supporting the plug and packing adjusting yokes (not shown) and surrounds a thrust collar 32. The thrust collar 32 has a cylindrical portion 33 surrounding the stem 34 of the plug 25, and further has a thrust washer portion 36 which bears on an annular top gasket 38. The gasket 38 bears on a sealing surface 39 (FIG. 4) surrounding the stem 34 at the top of the plug 25.

The plug 25 includes means therein defining passages in non-intersecting relation to the through port 28 providing for the flow of sterilizing steam therethrough. For this purpose, the plug 25 is provided with a pair of generally vertically extending internal steam passages 40 and 42 which extend substantially the length of the plug, as best shown in FIGS. 3 and 4. The passages 40 and 42 extend generally longitudinally of the plug and in non-intersecting relation to the through port 28. In the embodiment of FIGS. 1-5, the passages, at their upper extremeties, and immediately radially outward of the land sealing surface 38 open into the space immediately above the plug through a plurality of inlet openings, as best shown in FIGS. 3 and 4. A first set of inlet openings 44 extend into the passage 40 from the plug top and a second set 46 admits steam into the parallel passage 42. The steam flows downwardly through these passages and accumulates at a common region 48 at the bottom of the plug, and into the space 29.

Means in the casing 12 for admitting sterilizing steam into the passages formed in the plug includes an inlet opening 50 (FIG. 2) which extends into the casing interior between the top gasket 39 and the top 45 of the plug. The steam will enter the passage pairs 40 and 42 through the openings 44 and 46, and exit into the common opening 48 as shown by the arrows in FIG. 3. The bottom wall 52 of the casing 12 is provided with a steam outlet opening 55 (FIGS. 1 and 2) through which the steam is withdrawn.

In a typical installation, it is desirable to heat the valve components up to approximately 250° F. and hold the temperature for about 15 minutes to provide for complete sterilization. For this purpose, saturated steam at 50 psi and 297° F. may be used and applied to the inlet 50. It will noted that the position of the plug 25 is immaterial and the same may be either in the open or closed position. After about 15 minutes of application of such saturated steam, the entire interior surfaces of the valve 10 are sterilized by reason of the heat introduced through the plug to sterilize the interior plug surfaces. The interior body surfaces which are inaccessible to direct steam heating are heated by conduction from the plug 25, and a proper sterilizing temperature may thus be reached in a relatively short period of time.

Figure 7:
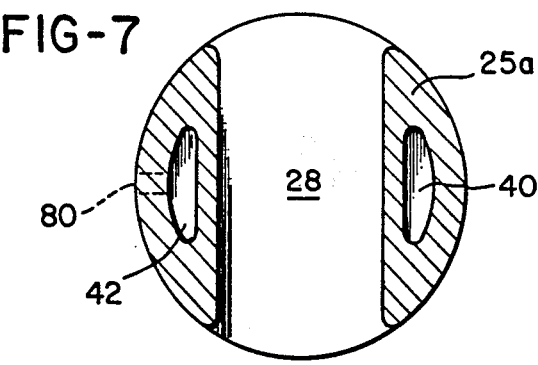
FIG. 7 is a transverse section through the valve plug looking generally along the line 7—7 of FIG. 6.

In some instances, it may be desirable to provide sterilizing steam to the interior downstream or outlet port 15 of the valve in order that the adjoining pipe line can be sterilized at the same time. For this purpose, the embodiment as shown in FIGS. 6 and 7 may be used where like parts are identified by like reference numerals. In this embodiment, the plug 25a does not include the groups of inlet openings 44 and 46 in the upper surface 45. Rather, an exit opening 80 is formed in the face surface of the plug in communication with the passage 42, and forms a steam outlet opening which opens into the valve outlet port 15 when the plug is in the closed position as shown in FIG. 6. Similarly, the inlet 50 is not used, but the outlet port 55 is now used as a steam inlet port, admitting steam into the valve plug interior 48 for flow into the passages 40 and 42, as shown by the arrows. While in this embodiment the passage 40 is deadended at the top of the plug, the velocity of steam flowing therein will cause the same to be directed upward and into the passage 40 and similarly upward and into the passage 42 and the excess steam will exit through the opening 80 into the outlet port 15 so that the steam may exit and sterilize the connected piping or plumbing attached to this port.

While the forms of apparatus herein described constitute preferred embodiments of this invention, it is to be understood that the invention is not limited to these precise forms of apparatus, and that changes may be made therein without departing from the scope of the invention which is defined in the appended claims.

What is claimed is:

1. A plug valve providing internal sterilization of the plug without diassembly, including a casing having a plug cavity and inlet and an outlet port opening into said cavity, a plug having upper and lower end surfaces and a side wall, said plug received in said casing having a through port through said side wall selectively alignable with said casing ports, and seal means in said casing cooperating with said plug side wall and isolating said ports with respect to said plug, the improvement comprising:

means in said plug defining a pair of steam passages extending generally longitudinally through the interior of said plug in non-intersecting and adjacent relation to said through port, one each of said steam passages on each side of said through port, and each said passage opening at one of said plug end surfaces, means in said casing for conducting sterilizing steam to said pair of passages at said one plug end surface for sterilizing the exterior of the plug, the through port, and the seal means by heat conduction without direct steam sterilization being applied to the exterior of the plug, the through port, and the seal means to prevent the possibility of contamination, and means in said casing for removing steam from said passages.

2. The valve of claim 1 in which said pair of passages open at said upper and lower end surfaces of said plug and in which said casing is provided with a steam inlet which opens into the valve interior adjacent said upper surface of said plug and a steam outlet which opens into the valve interior adjacent said lower surface of said plug.

3. The valve of claim 1 further comprising means in said plug defining a common recess at said plug lower surface opening into each of said steam passages, and said casing having a bottom closure wall spaced from said plug at said common recess, and having means in said bottom closure wall forming a steam passage opening into said recess.

* * * * *